United States Patent [19]

Bundy

[11] 4,313,877

[45] Feb. 2, 1982

[54] 11A-METHANO TXA$_2$ AMIDES

[75] Inventor: Gordon L. Bundy, Portage, Mich.

[73] Assignee: The Upjohn Company, Kalamazoo, Mich.

[21] Appl. No.: 116,115

[22] Filed: Jan. 28, 1980

Related U.S. Application Data

[62] Division of Ser. No. 35,143, May 1, 1979, Pat. No. 4,218,378.

[51] Int. Cl.$^3$ .................. C07D 305/14; C07D 405/02; C07D 407/02

[52] U.S. Cl. ................................ 260/333; 260/239 B; 260/239 BF; 260/326.5 D; 542/416; 542/417; 542/418; 542/421; 542/426; 542/429; 542/430; 542/431; 544/147; 544/376; 546/196; 546/269

[58] Field of Search ............... 542/416, 417, 418, 421, 542/426, 429, 430, 431; 546/269, 196; 544/147, 376; 260/239 B, 239 BF, 326.5 D, 333

[56] References Cited

U.S. PATENT DOCUMENTS 4,107,427 8/1978 Kelly ............................. 542/426

Primary Examiner—Arthur P. Demers
Attorney, Agent, or Firm—Robert A. Armitage

[57] ABSTRACT

The present invention provides novel thromboxane analogs and intermediates. Particularly, the present invention provides novel 11a-methano-TXA$_2$ amides.

3 Claims, No Drawings

11A-METHANO TXA2 AMIDES

CROSS REFERENCE TO RELATED APPLICATION

The present application is a division of Ser. No. 35,143, filed May 1, 1979, now U.S. Pat. No. 4,218,378.

BACKGROUND OF THE INVENTION

The present invention provides novel thromboxane analogs and intermediates. Particularly, the present invention provides novel 11a-methano-TXA$_2$ amides The essential material constituting a disclosure of the preparation and use of the compounds described above is incorporated here by reference from the U.S. Ser. No. 35,143, now U.S. Pat. No. 4,218,378.

PRIOR ART

As indicated above, thromboxane A$_2$ is known in the art. See Hamberg, M., et al., Proceedings of the National Academy of Sciences USA 72:2994 (1975), Samuelsson, Proceedings of the National Academy of Sciences USA 71:3400-3404 (1974). Likewise, numerous analogs of thromboxane B$_2$ and their use as reproductive cycle control agents is known in the art. See U.S. Pat. No. 4,070,384, issued Jan. 24, 1978.

Other heterocyclic ring analogs of the prostaglandins include the 9α,11α- or 11α,9α-epoxymethano-9,11-dideoxy-PGF-type compounds described in U.S. Pat. Nos. 3,950,363 and 4,028,354. Finally related azo and epoxyimino compounds are known in the art. See U.S. Pat. No. 4,112,224.

SUMMARY OF THE INVENTION

The present invention particularly provides a thromboxane analog of formula XI

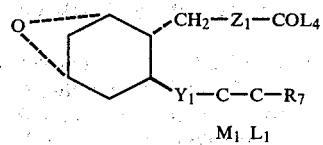

wherein Y$_1$ is
(1) trans—CH=CH—,
(2) cis—CH=CH—,
(3) —CH$_2$CH$_2$—, or
(4) —C≡C—,
wherein M$_1$ is α-R$_5$:β-OH, α-OH:β-R$_5$, or α-H:β-H, wherein R$_5$ is hydrogen or methyl, and wherein L$_1$ is α-R$_3$:β-R$_4$, α-R$_4$:β-R$_3$, or a mixture of α-R$_3$:β-R$_4$ and β-R$_3$:α-R$_4$, wherein R$_3$ and R$_4$ are hydrogen, methyl, or fluoro, being the same or different, with the proviso that one of R$_3$ and R$_4$ is fluoro only when the other is hydrogen or fluoro, or wherein —C(M$_1$)—C(L$_1$)—is trans—CH=CH—;
wherein Z$_1$ is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,
(7) —(CH$_2$)$_2$—O—CH$_2$—(CH$_2$)$_g$—CH$_2$—, or
(8) trans—CH$_2$—(CH$_2$)$_g$—CH$_2$—CH=CH—;
(9) —(m—Ph)—O—(CH$_2$)$_g$—, or
(10) —(m—Ph)—CH$_2$—(CH$_2$)$_g$—,
wherein g is one, 2, or 3 and —(m—Ph)— is meta-phenylene;
wherein R$_7$ is
(1) —(CH$_2$)$_m$—CH$_3$, wherein m is an integer from one to 5, inclusive;
(2) phenoxy;
(3) phenoxy substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that R$_7$ is phenoxy or substituted phenoxy, only when R$_3$ and R$_4$ are hydrogen or methyl, being the same or different; and
wherein L$_4$ is
(a) amino of the formula —NR$_{21}$R$_{22}$
wherein R$_{21}$ and R$_{22}$ are
(i) hydrogen;
(ii) alkyl or one to 12 carbon atoms, inclusive;
(iii) cycloalkyl of 3 to 10 carbon atoms, inclusive;
(iv) aralkyl of 7 to 12 carbon atoms, inclusive;
(v) phenyl;
(vi) phenyl substituted with one, 2, or 3 chloro, alkyl of one to three carbon atoms, inclusive, hydroxy, carboxy, alkoxycarbonyl of one to 4 carbon atoms, inclusive, or nitro;
(vii) carboxyalkyl of 2 to 5 carbon atoms, inclusive;
(viii) carbamoylalkyl of 2 to 5 carbon atoms, inclusive;
(ix) cyanoalkyl of 2 to 5 carbon atoms, inclusive;
(x) acetylalkyl of 3 to 6 carbon atoms, inclusive;
(xi) benzoylalkyl of 7 to 11 carbon atoms, inclusive;
(xii) benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
(xiii) pyridyl;
(xiv) pyridyl substituted by one, 2, or 3 chloro, alkyl of one to 3 carbon atoms, inclusive, or alkoxy of one to 3 carbon atoms, inclusive;
(xv) pyridylalkyl of 6 to 9 carbon atoms, inclusive;
(xvi) pyridylalkyl substituted by one, 2, or 3 chloro, alkyl of one to 3 carbon atoms, inclusive, hydroxy or alkoxy of one to 3 carbon atoms, inclusive;
(xvii) hydroxyalkyl of one to 4 carbon atoms, inclusive;
(xviii) dihydroxyalkyl of one to 4 carbon atoms, or
(xix) trihydroxyalkyl of one to 4 carbon atoms;
with the further proviso that not more than one of R$_{21}$ and R$_{22}$ is other than hydrogen or alkyl;
(b) cycloamino selected from the group consisting of
(i) pyrrolidino, (ii) piperidino
(iii) morpholino,
(iv) piperazino,
(v) hexamethyleneimino,
(vi) pyrrolino,
(vii) 3,4-didehydropiperidinyl, or
(viii) pyrrolidino, piperidino, morpholino, piperazino, hexamethyleneimino, pyrrolino, or 3,4-didehydropiperidinyl substituted by one or two alkyl of one to 12 carbon atoms, inclusive;
(c) carbonylamino of the formula —$NR_{23}COR_{21}$, wherein $R_{23}$ is hydrogen or alkyl of one to 4 carbon atoms and $R_{21}$ is other than hydrogen, but otherwise as defined above; or
(d) sulfonylamino of the formula —$NR_{23}SO_2R_{21}$, wherein $R_{21}$ and $R_{23}$ are as defined in (c);
(4) —$CH_2NL_2L_3$, wherein $L_2$ and $L_3$ are hydrogen or alkyl of one to 4 carbon atoms, inclusive, being the same or different, or a pharmacologically acceptable acid addition salt thereof wherein $X_1$ is —$CH_2NL_2L_3$.

DESCRIPTION OF PREFERRED EMBODIMENTS

The specific embodiments of the present invention include:
11a-methano-$TXA_2$, amide;
11a-methano-15-deoxy-$TXA_2$, amide.

The novel 11a-methano-TXA analogs of the present invention are all highly active as inhibitors of thromboxane synthetase and accordingly are useful for anti-inflammatory, anti-asthma and anti-thrombotic indications.

I claim:
1. A thromboxane analog of formula IV

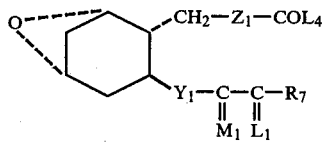

wherein $Y_1$ is
(1) trans—CH=CH—,
(2) cis—CH=CH—,
(3) —$CH_2CH_2$—, or
(4) —C≡C—,
wherein $M_1$ is α—$R_5$:β—OH, α—OH:β—$R_5$, or α—H:-β—H, wherein $R_5$ is hydrogen or methyl; and wherein $L_1$ is α—$R_3$:β—$R_4$, α—$R_4$:β$R_3$, or a mixture of α—$R_3$:β—$R_4$ and β—$R_3$:α—$R_4$, wherein $R_3$ and $R_4$ are hydrogen, methyl, or fluoro, being the same or different, with the proviso that one of $R_3$ and $R_4$ is fluoro only when the other is hydrogen or fluoro, or wherein —C($M_1$)—C($L_1$)— is trans—CH=CH—;
wherein $Z_1$ is
(1) cis—CH=CH—$CH_2$—$(CH_2)_g$—$CH_2$—,
(2) cis—CH=CH—$CH_2$—$(CH_2)_g$—$CF_2$—,
(3) cis—$CH_2$—CH=CH—$(CH_2)_g$—$CH_2$—,
(4) —$(CH_2)_3$—$(CH_2)_g$—$CH_2$—,
(5) —$(CH_2)_3$—$(CH_2)_g$—$CF_2$—,
(6) —$CH_2$—O—$CH_2$—$(CH_2)_g$—$CH_2$—,
(7) —$(CH_2)_2$—O—$(CH_2)_g$—$CH_2$—,
(8) trans—$CH_2$—$(CH_2)_g$—$CH_2$—CH=CH—,
(9) —(m—Ph)—O—$(CH_2)_g$—, or
(10) —(m—Ph)—$CH_2$—$(CH_2)_g$—,
wherein g is one, 2, or 3 and —(m—Ph)— is meta-phenylene;

wherein $R_7$ is
(1) —$(CH_2)_m$—$CH_3$, wherein m is an integer from one to 5, inclusive;
(2) phenoxy;
(3) phenoxy substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different; and
wherein $L_4$ is
(a) amino of the formula —$NR_{21}R_{22}$, wherein $R_{21}$ and $R_{22}$ are
(i) hydrogen;
(ii) alkyl of one to 12 carbon atoms, inclusive;
(iii) cycloalkyl of 3 to 10 carbon atoms, inclusive;
(iv) aralkyl of 7 to 12 carbon atoms, inclusive;
(v) phenyl;
(vi) phenyl substituted with one, 2, or 3 chloro, alkyl of one to three carbon atoms, inclusive, hydroxy, carboxy, alkoxycarbonyl of one to 4 carbon atoms, inclusive, or nitro;
(vii) carboxyalkyl of 2 to 4 carbon atoms, inclusive;
(viii) carbamoylalkyl of 2 to 5 carbon atoms, inclusive;
(ix) cyanoalkyl of 2 to 5 carbon atoms, inclusive;
(x) acetylalkyl of 3 to 6 carbon atoms, inclusive;
(xi) benzoylalkyl of 7 to 11 carbon atoms, inclusive;
(xii) benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
(xiii) pyridyl;
(xiv) pyridyl substituted by one, 2, or 3 chloro, alkyl of one to 3 carbon atoms, inclusive, or alkoxy of one to 3 carbon atoms, inclusive;
(xv) pyridylalkyl of 6 to 9 carbon atoms, inclusive;
(xvi) pyridylalkyl substituted by one, 2, or 3 chloro, alkyl of one to 3 carbon atoms, inclusive, hydroxy or alkoxy of one to 3 carbon atoms, inclusive;
(xvii) hydroxyalkyl of one to 4 carbon atoms, inclusive;
(xviii) dihydroxyalkyl of one to 4 carbon atoms, or
(xix) trihydroxyalkyl of one to 4 carbon atoms; with the further proviso that not more than one of $R_{21}$ and $R_{22}$ is other than hydrogen or alkyl;
(b) cycloamino selected from the group consisting of
(i) pyrrolidino,
(ii) piperidino,
(iii) morpholino,
(iv) piperazino, (v) hexamethyleneimino,
(vi) pyrrolino,
(vii) 3,4-didehydropiperidinyl, or
(viii) pyrrolidino, piperidino, morpholino, piperazino, hexamethyleneimino, pyrrolino, or 3,4-didehydropiperidinyl substituted by one or two alkyl of one to 12 carbon atoms, inclusive;
(c) carbonylamino of the formula $-NR_{23}COR_{21}$, wherein $R_{23}$ is hydrogen or alkyl of one to 4 carbon atoms and $R_{21}$ is other than hydrogen, but otherwise as defined above; or
(d) sulfonylamino of the formula $-NR_{23}SO_2R_{21}$, wherein $R_{21}$ and $R_{23}$ are as defined in (c).

2. 11a-Methano-$TXA_2$, amide, a thromboxane analog according to claim 1, wherein $L_4$ is $-NH_2$.

3. 11a-Methano-15-deoxy-$TXA_2$, amide, a thromboxane analog according to claim 1, wherein $L_4$ is $-NH_2$.